United States Patent
Carter et al.

(10) Patent No.: US 10,322,077 B2
(45) Date of Patent: *Jun. 18, 2019

(54) METHODS AND COMPOSITIONS FOR TATTOO REMOVAL

(71) Applicant: BioChemics, Inc., Danvers, MA (US)

(72) Inventors: Stephen G. Carter, Andover, MA (US); Zhen Zhu, Andover, MA (US); Kanu Patel, Londonderry, NH (US); Diane L. Kozwich, Nottingham, NH (US); Laura Stephens, Danvers, MA (US); John J. Masiz, Topsfield, MA (US); David H. Donabedian, Providence, RI (US)

(73) Assignee: BioChemics, Inc., Danvers, MA (US)

( * ) Notice: Subject to any disclaimer, the term of this patent is extended or adjusted under 35 U.S.C. 154(b) by 449 days.

This patent is subject to a terminal disclaimer.

(21) Appl. No.: 15/008,699

(22) Filed: Jan. 28, 2016

(65) Prior Publication Data

US 2016/0213586 A1 Jul. 28, 2016

Related U.S. Application Data

(63) Continuation of application No. 12/631,698, filed on Dec. 4, 2009, now Pat. No. 9,278,233.

(60) Provisional application No. 61/120,009, filed on Dec. 4, 2008.

(51) Int. Cl.
| | | |
|---|---|---|
| A61M 37/00 | (2006.01) | |
| A61K 8/49 | (2006.01) | |
| A61B 18/20 | (2006.01) | |
| A61K 8/02 | (2006.01) | |
| A61K 8/67 | (2006.01) | |
| A61Q 1/14 | (2006.01) | |
| A61Q 19/02 | (2006.01) | |
| A61K 8/26 | (2006.01) | |
| A61K 8/34 | (2006.01) | |
| A61K 8/58 | (2006.01) | |
| A61K 8/73 | (2006.01) | |
| A61K 8/92 | (2006.01) | |
| A61B 17/00 | (2006.01) | |
| A61B 18/00 | (2006.01) | |
| A61N 1/32 | (2006.01) | |
| A61N 5/06 | (2006.01) | |

(52) U.S. Cl.
CPC .......... *A61K 8/4926* (2013.01); *A61B 18/203* (2013.01); *A61K 8/0208* (2013.01); *A61K 8/26* (2013.01); *A61K 8/342* (2013.01); *A61K 8/498* (2013.01); *A61K 8/585* (2013.01); *A61K 8/678* (2013.01); *A61K 8/73* (2013.01); *A61K 8/922* (2013.01); *A61Q 1/145* (2013.01); *A61Q 19/02* (2013.01); *A61B 2017/00769* (2013.01); *A61B 2018/0047* (2013.01); *A61B 2018/00452* (2013.01); *A61K 2800/51* (2013.01); *A61K 2800/74* (2013.01); *A61K 2800/81* (2013.01); *A61K 2800/91* (2013.01); *A61M 37/0092* (2013.01); *A61N 1/325* (2013.01); *A61N 5/062* (2013.01)

(58) Field of Classification Search
CPC ........ A61B 18/203; A61B 2017/00769; A61B 2018/00452; A61N 5/062; A61Q 1/145
See application file for complete search history.

(56) References Cited

U.S. PATENT DOCUMENTS

| | | | |
|---|---|---|---|
| 4,440,777 A | 4/1984 | Zupan | 424/274 |
| 4,758,599 A | 7/1988 | Minetti | 514/844 |
| 4,830,856 A | 5/1989 | Peppers | 424/449 |
| 4,933,184 A | 6/1990 | Tsuk | 424/449 |
| 5,229,130 A | 7/1993 | Sharma et al. | 424/449 |
| 5,451,407 A | 9/1995 | Cormier et al. | 424/448 |
| 5,460,821 A | 10/1995 | Masiz | 424/449 |
| 5,496,827 A | 3/1996 | Patrick | 514/310 |
| 5,527,530 A | 6/1996 | Simmons et al. | 424/401 |
| 5,645,854 A | 7/1997 | Masiz | 424/449 |
| 5,853,751 A | 12/1998 | Masiz | 424/449 |
| 5,874,074 A * | 2/1999 | Smith | A61K 9/08 424/401 |
| 5,895,649 A | 4/1999 | De Lacharriere et al. | 424/130.1 |
| 5,895,658 A | 4/1999 | Fossel | 424/401 |
| 5,922,332 A | 7/1999 | Fossel | 424/401 |
| 5,932,215 A | 8/1999 | de Lacharriere et al. | 424/158.1 |
| 5,980,882 A | 11/1999 | Eichman | 424/78.12 |
| 6,207,713 B1 | 3/2001 | Fossel | 514/565 |
| 6,306,130 B1 | 10/2001 | Anderson et al. | 606/27 |
| 6,321,909 B1 | 11/2001 | Wicomb et al. | 206/438 |
| 6,458,841 B2 | 10/2002 | Fossel | 514/565 |
| 6,477,410 B1 | 11/2002 | Henley et al. | 604/20 |
| 6,486,206 B1 | 11/2002 | Lurie | 514/561 |

(Continued)

FOREIGN PATENT DOCUMENTS

| | | | | |
|---|---|---|---|---|
| EP | 1 621 192 A1 | 2/2006 | | A61K 31/192 |
| WO | WO 01/17498 A1 | 3/2001 | | A61K 7/48 |

(Continued)

OTHER PUBLICATIONS

Baumler, et al., "Q-Switch Laser and Tattoo Pigments: First Results of the Chemical and Photophysical Analysis of 41 Compounds," Lasers in Surgery and Medicine, vol. 26, pp. 13-21, 2000.

(Continued)

*Primary Examiner* — Laura A Bouchelle
(74) *Attorney, Agent, or Firm* — Sunstein Kann Murphy & Timbers LLP

(57) ABSTRACT

Methods and formulations for removing a tattoo by using a cell disrupter in combination with a vasodilator, and optionally one or more of an osmotic modifying agent, a chelation agent, and an occlusive modifying agent. Embodiments optionally further include using one or more of an antibiotic, anesthetic, penetration enhancer, excipient, carrier and vehicle.

17 Claims, No Drawings

(56) References Cited

U.S. PATENT DOCUMENTS

| | | | | |
|---|---|---|---|---|
| 6,527,716 | B1 | 3/2003 | Eppstein | 600/309 |
| 6,635,274 | B1 | 10/2003 | Masiz et al. | 424/449 |
| 6,735,470 | B2 | 5/2004 | Henley et al. | 604/20 |
| 7,041,657 | B2 | 5/2006 | Vournakis et al. | 514/62 |
| 7,041,677 | B2 | 5/2006 | Cutler | 514/312 |
| 7,069,073 | B2 | 6/2006 | Henley et al. | 604/20 |
| 7,105,172 | B1 | 9/2006 | Bolla | 424/400 |
| 7,115,588 | B2 | 10/2006 | Vournakis et al. | 514/62 |
| 7,179,253 | B2 * | 2/2007 | Graham | A61B 18/203 128/898 |
| 7,179,789 | B2 | 2/2007 | Patt | 514/6 |
| 7,192,616 | B2 | 3/2007 | Cals-Grierson et al. | 424/769 |
| 7,604,797 | B2 | 10/2009 | Hicks | 424/78.06 |
| 9,278,233 | B2 * | 3/2016 | Carter | A61B 18/203 |
| 2003/0091659 | A1 | 5/2003 | Lu et al. | 424/727 |
| 2003/0104043 | A1 | 6/2003 | Brown et al. | 424/450 |
| 2003/0206946 | A1 | 11/2003 | Chung | 424/450 |
| 2004/0181211 | A1 | 9/2004 | Graham et al. | 606/9 |
| 2005/0042270 | A1 | 2/2005 | Aldred | 424/449 |
| 2005/0065503 | A1 * | 3/2005 | Anderson | A61B 18/203 606/9 |
| 2005/0201959 | A1 * | 9/2005 | David | A61K 38/20 424/62 |
| 2005/0256204 | A1 | 11/2005 | Bitter, Sr. | 514/649 |
| 2005/0271596 | A1 | 12/2005 | Friedman et al. | 424/45 |
| 2006/0057081 | A1 | 3/2006 | Boxrud | 424/59 |
| 2006/0062836 | A1 | 3/2006 | Carter et al. | 424/449 |
| 2006/0217690 | A1 | 9/2006 | Bastin et al. | 606/9 |
| 2007/0078448 | A1 | 4/2007 | Lipman | 606/9 |
| 2007/0166252 | A1 * | 7/2007 | Hattendorf | A61K 8/02 424/62 |
| 2007/0178121 | A1 | 8/2007 | First et al. | 424/239.1 |
| 2008/0009774 | A1 | 1/2008 | Capelli et al. | 601/3 |
| 2008/0044439 | A1 | 2/2008 | David | 424/239.1 |
| 2008/0112909 | A1 | 5/2008 | Faler et al. | 424/61 |
| 2008/0312296 | A1 | 12/2008 | Carter et al. | 514/356 |
| 2009/0053290 | A1 | 2/2009 | Sand et al. | 424/449 |
| 2009/0221536 | A1 | 9/2009 | Fossel | 514/162 |
| 2009/0227936 | A1 * | 9/2009 | Pellegrini | A61B 18/203 604/20 |
| 2010/0003353 | A1 | 1/2010 | Stephens et al. | 424/744 |
| 2010/0076035 | A1 | 3/2010 | Carter et al. | 514/365 |

FOREIGN PATENT DOCUMENTS

| | | | |
|---|---|---|---|
| WO | WO 02/22120 A1 | 3/2002 | A61K 31/275 |
| WO | WO 03/076600 A2 | 9/2003 | C12N 5/00 |
| WO | WO 2003/076600 A3 | 9/2003 | C12N 5/00 |
| WO | WO 2005/051365 A1 | 6/2005 | A61K 9/70 |
| WO | WO 2005/091891 | 10/2005 | |
| WO | WO 2005/102282 | 11/2005 | A61K 9/14 |
| WO | WO 2005/123190 A1 | 12/2005 | A61N 7/00 |
| WO | WO 2006/104660 | 10/2006 | A61L 15/30 |
| WO | WO 2007/086395 A1 | 8/2007 | A61K 45/06 |
| WO | WO 2007/103555 | 9/2007 | A61K 8/49 |
| WO | WO 2008/054059 | 5/2008 | A61K 31/35 |
| WO | WO 2008/109124 | 9/2008 | A61K 31/21 |
| WO | WO 2008/156758 | 12/2008 | A61K 31/74 |
| WO | WO 2009/111075 | 9/2009 | A61N 5/06 |

OTHER PUBLICATIONS

Bernstein, "Laser treatment of tattoos," Clinics in Dermatology, vol. 24, No. 1, pp. 43-55, Jan. 2006.

Christensen, et al., "The ultrastructure of tattoo marks," Acta pathologica et microbiologica Scandinavica, Section A, vol. 80, No. 4, pp. 573-576, 1972.

Elsaie, et al., "Topical imiquimod in conjunction with Nd:YAG laser for tattoo removal," Lasers Med. Sci., vol. 24, No. 6, pp. 871-875, 2009.

Ferguson, et al., "The Q-switched neodymium: YAG laser and tattoos: a microscopic analysis of laser-tattoo interactions," British Journal of Dermatology, vol. 137, pp. 405-410, 1997.

Ferndale Pharmaceuticals Ltd., "LMX4 lidocaine 4% w/w cream," Summary of Product Characteristics, 5 pages, Revised 2010.

Goldberg, "Laser Treatment of Vascular Lesions," Clinics in Plastic Surgery, vol. 27, No. 2, pp. 173-180, Apr. 2000.

Jesitus, "Latest advances: Triple-pass rosacea laser tx," Dermatology Times, 2 pages, Mar. 2005.

Jesitus et al., "Latest Advances in Rosacea Treatment: Triple-Pass Laser Treatment," Dermatology Times, 4 pages, updated: Jun. 1, 2005.

Kautz et al., "Management of Rosacea with Intense Pulsed Light (IPL) Systems and Laser," Medical Laser Application, vol. 23, No. 2, pp. 65-70, 2008.

Kilmer, et al., "Clinical Use of the Q-Switched Ruby and the Q-Switched Nd:YAG (1064 nm and 532 nm) Lasers for Treatment of Tattoos," The Journal of Dermatologic Surgery and Oncology, vol. 19, No. 4, pp. 330-338, 1993.

Lea, et al., "Human tattoo. Electron Microscopic Assessment of Epidermis, Epidermal-Dermal Junction, and Dermis," International Journal of Dermatology, vol. 26, No. 7, pp. 453-458, 1987.

McGill et al., "The Effect of Ambient Temperature on Capillary Vascular Malformations," British Journal of Dermatology, vol. 154, No. 5, pp. 896-903, 2006.

Newton et al., "Mechanisms influencing the vasoactive effects of lidocaine in human skin," Anaesthesia, vol. 62, No. 2, pp. 146-150, 2007.

Osuka, et al., "Vasodilator Effects on Canine Basilar Artery Induced by Intracisternal Interleukin-1β," Journal of Cerebral Blood Flow and Metabolism, vol. 17, pp. 1337-1345, 1997.

Ricotti, et al., "Laser-Assisted Tattoo Removal with Topical 5% Imiquimod Cream," Dermatologic Surgery, vol. 33, No. 9, pp. 1082-1091, 2007.

Solis, et al., "Experimental Nonsurgical Tattoo Removal in a Guinea Pig Model with Topical Imiquimod and Tretinoin," Dermatol. Surg., vol. 28, pp. 83-87, 2002.

Svaasand et al., "Increase of Dermal Blood Volume Fraction Reduces the Threshold for Laser-Induced Purpura: Implications for Port Wine Stain Laser Treatment," Lasers in Surgery and Medicine, vol. 34, No. 2, pp. 182-188, 2004.

Taylor, et al., "Light and Electron Microscopic Analysis of Tattoos Treated by Q-Switched Ruby Laser," J. Invest. Dermatol., vol. 97, No. 1, pp. 131-136, 1991.

Wheeland, "Clinical Uses of Lasers in Dermatology," Lasers in Surgery and Medicine, vol. 16, No. 1, pp. 2-23, 1995.

WiseAcre Gardens, Bugleweed—Perennials: Ajuga reptans, Found http://www.wiseacre-gardens.com/plants/perennial/buglewwed. html, 3 pages, Oct. 2010.

Zelickson, et al., "Clinical, Histologic, and Ultrastructural Evaluation of Tattoos Treated with Three Laser Systems," Lasers in Surgery and Medicine, vol. 15, No. 4, pp. 364-372, 1994.

European Patent Office, International Search Report, including the Written Opinion of the International Searching Authority—International Application No. PCT/US2009/047098, 10 pages, dated Aug. 27, 2009.

European Patent Office, International Search Report, together with the Written Opinion of the International Searching Authority—International Application No. PCT/US2009/057916, 12 pages, dated Feb. 1, 2010.

European Patent Office, International Search Report, including the Written Opinion of the International Searching Authority—International Application No. PCT/US2009/066865, 15 pages, dated Jul. 15, 2011.

European Patent Office, International Preliminary Report on Patentability, including the Written Opinion of the International Searching Authority—International Application No. PCT/US2009/066865, 8 pages, dated Sep. 20, 2011.

European Patent Office, EPO Communication pursuant to Rules 161(1) and 162 EPC—Application No. EP 09764427.2, 2 pages, dated Nov. 21, 2011.

Schlich LLP in the name of BioChemics, Inc., Response pertaining to EPO Communication under Rules 161(1) and 162 EPC—Application No. EP 09764427.2, 4 pages, dated Jun. 1, 2012.

(56) References Cited

OTHER PUBLICATIONS

European Patent Office, Office Action for Application No. 09 764 427.2-1458 pursuant to Article 94(3) EPC, 6 pages, dated Jul. 14, 2015.
European Patent Office, Communication pursuant to Article 94(3) EPC, Application No. 09764427.2-1458, 5 pages, dated Dec. 6, 2016.
United States Patent and Trademark Office, Restriction Requirement Office Action, pertaining to U.S. Appl. No. 12/564,841, 7 pages, dated Oct. 20, 2011.
Sunstein Kann Murphy & Timbers LLP Response pertaining to U.S. Appl. No. 12/564,841, 13 pages, dated Dec. 20, 2011.
United States Patent and Trademark Office, Office Action pertaining to U.S. Appl. No. 12/564,841, 35 pages, dated Jan. 20, 2012.
Sunstein Kann Murphy & Timbers LLP, Response pertaining to U.S. Appl. No. 12/564,841, 45 pages, dated Apr. 8, 2012.
United States Patent and Trademark Office, Office Action pertaining to U.S. Appl. No. 12/564,841, 18 pages, dated Aug. 16, 2012.
United States Patent and Trademark Office, Applicant-Initiated Interview Summary pertaining to U.S. Appl. No. 12/564,841, 3 pages, dated Sep. 17, 2012.
United States Patent and Trademark Office, Applicant-Initiated Interview Summary pertaining to U.S. Appl. No. 12/564,841, 3 pages, dated Oct. 26, 2012.

* cited by examiner

METHODS AND COMPOSITIONS FOR TATTOO REMOVAL

REFERENCE TO RELATED APPLICATION

This application is a continuation application of U.S. non-provisional application Ser. No. 12/631,698 filed Dec. 4, 2009 which itself claims benefit of U.S. provisional application Ser. No. 61/120,009, filed Dec. 4, 2008, the entire contents of which are hereby incorporated by reference.

TECHNICAL FIELD

The present invention relates to tattoo removal.

BACKGROUND

It is estimated that 50% of the 20 million people in the western world with tattoos are interested in having the tattoos removed. Methods of tattoo removal have been developed, but those methods are often ineffective, take a long period of time, and involve considerable pain.

Professional tattoos are created by injecting tattoo inks with a rapidly reciprocating needle that drives ink particles into the dermis to a depth of 0.6 mm to 2.2 mm. The inks used in tattooing are derived from exogenous pigments, most of unknown purity. Pigments in tattoo ink include iron oxides, chromium oxide, aluminum oxide, titanium oxide, barium sulfate, zinc oxide, sodium copper silicate, sodium aluminum silicate, copper carbonate, dioxazine and carbazole. Following injection, the ink pigment particles reside in the interstitial space between dermal cells where they form large aggregates of about 140 µm to 180 µm until fibroblasts or macrophages engulf the pigment particles and internalize the tattoo ink into the skin cells. The size of the ink particle aggregates and the collagen network surrounding the aggregates help keep the ink pigments within the skin making the tattoo permanent, thus the difficulty with removal of tattoos.

The most popular method for removing unwanted tattoos is the laser method, which delivers short pulses of intense light that pass through the epidermis to be selectively absorbed by the tattoo pigment in the dermis. The lasers developed specifically for use in tattoo removal use a technique known as Q-switching, which refers to the laser's short, high-energy pulses. The lasers typically used are a Q-switched frequency doubled Nd:YAG laser (532 nm) for red orange and purple pigment; a Q-switched Nd:YAG laser (1064 nm) for black pigment; a Q-switched ruby laser (694 nm) for black pigment; and a Q-switched alexandrite laser (755 nm) for blue and green pigment.

The mechanism by which Q-switched lasers remove tattoos involves selective rupture of the skin cells, breakdown of tattoo ink particle aggregates, and ink removal by trans-epidermal elimination and/or lymphatic transport (Taylor et al., J. Invest. Dermatol., 97:131-136 (1991); Ferguson et al., Br. J. Dermatol., 137:405-410 (1997)). Although the human immune system is able to remove some of the pigment fragments, causing fading of the tattoo (Wheeland, Lasers in Surgery and Medicine 16:2 23 (1995); Zelickson et al., Lasers in Surgery and Medicine 15:364 372 (1994)), most pigment fragments become re-phagocytosed by still intact dermal cells and so the tattoo remains visible (Ferguson et al., British Journal of Dermatology 137:405 410 (1997)).

Laser treatments must be spaced at least one month apart because the laser causes a painful burn to form on the skin. Laser treatments may not completely remove a mature tattoo, and are expensive, time consuming, and painful.

SUMMARY

An embodiment of the present invention provides a method of removing a tattoo from a region of skin; the embodiment includes treating the region with a cell disruptor (e.g., a laser) and administering to the same region a composition comprising a vasodilator to cause enlargement of blood vessels in the region, so that combined action of the composition and the cell disruptor causes removal of the tattoo. In a further related embodiment, the composition further comprises at least one osmotic modifying agent. Alternatively, or in addition, the composition includes at least one chelating agent. In a further related embodiment, administering the composition includes applying it topically to the region. Alternatively or in addition, administering the composition includes applying it via a transdermal patch. Administering the composition may include injecting it into the region with a suitable medical device. In a further related embodiment, injecting the composition includes using a hypodermic needle, a syringe, or a needleless injection device. Alternatively or in addition, administering the composition includes delivering it by any combination of a topical formulation, a patch-like device, an iontophoresis device, a sonophoresis device, and an injection. Alternatively or in addition, administering the composition includes covering the region with a non-breathable occlusive barrier that dries on the skin. In a further related embodiment, covering with the occlusive barrier includes using a physical non-breathable layer. In a further related embodiment, treating the region with the cell disruptor includes using externally applied energy. Optionally, treating the region with the cell disruptor includes using a laser.

In a further related embodiment, treating the region with the cell disruptor includes using externally applied derived energy selected from at least one of a thermal, sonic, ultrasound, visible light, infrared light, ultraviolet light, electric, magnetic, chemical, enzymatic, and mechanical energy, and other type of energy.

In a further related embodiment, treating the region with the cell disruptor takes place after administering the composition. Alternatively or in addition, treating the region with the cell disruptor takes place before administering the composition. Alternatively or in addition, treating the region with the cell disruptor takes place coincident with administering the composition. In a further related embodiment, administering the composition occurs in a single dose. Alternatively, administering the composition occurs in one of multiple doses and multiple times per day.

In another related embodiment, administering the composition includes administering it to one of a human and a non-human animal.

DETAILED DESCRIPTION

Applicants have invented methods and formulations for removing a tattoo by using a cell disruptor in combination with a vasodilator, and optionally one or more of an osmotic modifying agent, a chelation agent, and an occlusive modifying agent. The tattoo may be removed more effectively using this combination treatment than can be achieved using prior methods. Embodiments optionally further include using one or more of an antibiotic, anesthetic, penetration enhancer, excipient, carrier, and vehicle.

The vasodilator enlarges blood vessels and causes fluid extravasation, so that the fluid leaks from the vessel into interstitial spaces in the skin. The cell disruptor either causes the cells of the skin to rupture, or the cells of the skin to release dye particulates, or both, thereby releasing ink particles from intracellular compartments into the interstitial spaces of the tissue. As a result of the action of the cell disruptor and the associated energy upon administration, the liberated ink particles may be broken down or disintegrated. The extra fluid in the tissue resulting from the action of the vasodilator serves as a force to move the ink particles and helps to carry away the ink particles from the skin tissue, so that the composition and the cell disruptor act together to enhance removal of the tattoo.

Definitions

As used in this description and the accompanying claims, the following terms shall have the meanings indicated, unless the context otherwise requires:

A "tattoo" is a portion of skin in which tattoo ink has been embedded.

"Removing" a tattoo from a region of skin means disembedding, for example by dislodging, tattoo ink from the region of tissue underlying or surrounding the tattoo, and includes dislodging and movement of the ink particles that is sufficient to cause some fading, with or without total elimination, of the tattoo. "Removal" of a tattoo from a region of skin similarly means having produced dislodgment of the tattoo ink from the tissue that is sufficient to cause some fading, with or without total elimination, of the tattoo.

A "cell disruptor" is an energy source, such as a laser (or thermal, sonic, electromagnetic or other energy), that causes ink of a tattoo to be released from skin cells.

A "vasodilator" is a substance that causes relaxation of the walls of the blood vessels which in turn results in an enlargement of the blood vessels.

An "osmotic modifying agent" is a composition having affinity for water to draw water from cells, vasculature or other structures of the skin.

A "chelating agent" is a small molecule that binds very tightly to metal ions.

An "occlusive barrier" is a component of a formulation, such as a solid patch or wrap, a hydrophobic chemical component, or a self-assembling chemical component, that reduces water loss due to transpiration when applied to the region.

"%" is used herein to refer to the concentration of a component expressed in a weight percent (% wt) basis.

The term "about", as it applies to concentration ranges, refers to both the upper and lower limit of the range. Where concentration ranges are included to provide guidance to those of ordinary skill in the art, the term "about" communicates that the range does not have absolute and critical limits unless other wise indicated.

Applicants have invented a formulation useful for enhancing the effectiveness of tattoo removal by cell disruption. The tattoo removal formulation includes a vasodilator, optionally combined with one or both of an osmotic modifying agent and chelation agent. Due to synergistic effects, the tattoo may be removed more effectively than would be achieved using prior art methods. Embodiments also include using one or more of an antibiotic, anesthetic, penetration enhancer, excipient, carrier or vehicle.

An embodiment of the present invention includes treating a region of skin with a cell disruptor, and administering to the region a composition formulated at least with a vasodilator. The vasodilator may enlarge blood vessels and causes fluid extravasation, so that the fluid leaks from the vessel into interstitial spaces in the skin. The cell disruptor may cause the cells to rupture so as to disembed, the ink particles, such as by releasing ink particles from intracellular compartments into the interstitial spaces of the tissue. As a result of the action of the cell disruptor and the associated energy upon administration, the liberated ink particles may be broken down or disintegrated. The extra fluid in the tissue resulting from the action of the vasodilator serves as a force to move the ink particles and helps to carry away the ink particles from the skin tissue, so that the composition and the cell disruptor together enhance removal of the tattoo.

In other embodiments, the method involves treating a region of skin with a cell disruptor and administering a composition formulated with a vasodilator and an osmotic modifying agent. The osmotic modifying agent may draw fluid from cells into the interstitial spaces of the skin. The resulting cell shrinkage creates more interstitial space and the extra fluid resulting from the action of the vasodilator may combine to help carry away ink aggregates from the skin tissue, so that the composition and the cell disruptor together enhance removal of the tattoo.

In other embodiments, the method involves treating a region of skin with a cell disruptor and administering a composition formulated with a vasodilator and a chelating agent. The chelating agent is thought to bind to metal ions in the ink particles produced as a result of fragmenting the ink aggregates with the cell disruptor. This binding event may prevent re-aggregation of the disintegrated ink particles following cell disruptor treatment, facilitating the removal of ink particles, so that the composition and the cell disruptor together enhance removal of the tattoo.

In yet other embodiments, the method includes treating a region of skin with a cell disruptor and administering a composition formulated with a vasodilator, an osmotic modifying agent and a chelating agent. In various embodiments, the components of the method may work together additively or synergistically to release ink particles from cells, break down ink aggregates, prevent re-aggregation of ink particles, enlarge the interstitial space, and increase the amount of fluid to move the particles away from the skin. In a related embodiment, the composition and the cell disruptor together enhance removal of the tattoo.

In one embodiment, the composition suitable for practicing the invention may include one or more additional active ingredients including an antibiotic, a pain reliever, or a skin penetration enhancer. In another embodiment, the composition may be delivered in formulation with any acceptable excipient, carrier, or vehicle.

Tattoo removal formulations can be delivered in a conventional topical dosage form such as, for example, a cream, an ointment, an aerosol formulation, a non-aerosol spray, a gel, a foam, a solution, a suspension, a dispersion, an emulsion, a micro-emulsion, a paste, a powder, a solid stick (e.g., wax- or petroleum-based sticks), a wipe, an oil, a lotion, or the like. In various embodiments, administering the composition includes delivering it by any one or a combination of a topical formulation, a patch-like device, an iontophoresis device, a sonophoresis device, and an injection. For ease of administration, a tattoo removal formulation is administered in a single composition. Alternatively, where preferred due to the chemical compatibility and interactions, or due to physical stability, components of a tattoo removal formulation can be packaged two or more separate compositions. The components are delivered to a patient simultaneously using a package similar to, for example, a multi-colored toothpaste tube, or using a tube or other delivery vehicle having more than one chamber. In a related embodiment, components of the different portions of the formulation can be mixed as they leave the tube or vehicle.

In one embodiment, the vasodilators include but are not limited, to one more of: L-arginine, methyl nicotinate, tolazoline, sodium nitroprusside, acetylcholine, and derivatives of these. Generally, a suitable formulation may contain, for example, about 0.001% to about 50% active vasodilator, preferably in the range of 0.01-0.5%, or up to 2%, 5%, 15% or 30%. In one embodiment, the vasodilator is methyl nicotinate, preferably at a range of about 0.01-0.5%. In another embodiment, acetylcholine is used in a range of about 0.1-1.0%. In another embodiment, sodium nitroprusside is used in a range of about 0.5 to about 3.0%. In another embodiment, tolazoline is used in a range of about 0.01% to about 0.3%.

The method can include allowing a wait time sufficient for the vasodilation composition to cause dilation of the affected, i.e., abnormal, blood vessels prior to introducing the energy, such time referred to herein as a "vasodilation time".

In the alternative or in combination with the above stated vasodilators, the tattoo removal formulation can include other active vasodilation ingredients known to those of ordinary skill in the art. Examples of such vasodilating agents include ginger extract, ginkgo biloba, hawthorne extract, bamethan sulphate, bencyclane fumarate, benpurodil hemisuccinate, benzyl nicotinate, buflomedil hydrochloride, buphenine hydrochloride, butalamine hydrochloride, cetledil citrate, ciclonicate, cinepazide maleate, cyclandelate, di-isopropylammonium dichloroacetate, ethyl nicotinate, hepronicate, hexyl nicotinate, Ifenprodil tartrate, inositol nicotinate, isoxsuprine hydrochloride, kallidinogenase, methyl nicotinate, maftidropuryl oxalate, nicametate citrate, niceritrol, nicobuxil, nicofuranose, nicotinyl alcohol, nicotinyl alcohol tartrate, nonidamide, oxpentifylline, papaveroline, pentifylline, pipratecol, propentofylline, raubasine, suloctidil, teasuprine, thymoxamine hydrochloride, tolazoline, xanthinol nicotinate, diazoxide, hydralazine, minoxidil, centrally acting agents including clonidine, quanaberz and methyl dopa, alpha-adrenoceptor agents including indoramin, phenoxybenzamine, phentolamine and prazosin, adrenergic neuron blocking agents including bethanidine, debrisoquine and guanethidine, ACE inhibitors including benazepril, captopril, cilazapril, enalapril, fosinopril, lisinopril, perindopril, quinapril and ramipril, ganglion-blocking agents including pentolinium and trimetaphan, calcium-channel blockers including amlodipine, diltiazem, felodipine, isradipine, nicardipine, nifedipine, nimodipine and verapamil, prosteglandins including prostacyclin, thrombuxane A2 leukotrienes, PGA, PGA1 PGA2 PGE1 PGE2 PGD, PGG and PGH, and angiotension II analogs including saralasin. Other suitable vasodilators include nitroglycerin, labetalol, thrazide, isosorbide dinitrate, pentaerythritol tetranitrate, digitalis, hydralazine, and diazoxide, in a concentration range of 0.001 to 50.0% w/w, e.g., 0.01% to 10.0% w/w.

In other embodiments, vasodilators are preferred that exhibit relative non-toxicity or safety for human administration. Relatively safe vasodilators can be used at higher concentrations than less safe vasodilators. By way of example, arginine has advantages for use as a vasodilator due to its relative non-toxicity. Arginine can be used at up to about 30%.

Osmotic modifying agents useful in tattoo removal formulations can include, without limitation, one or more of: mono and divalent ions including lithium, sodium, potassium, rubidium, cesium, beryllium, magnesium, calcium, iodine, strontium and barium; monosaccharides and disaccharides such as glucose, fructose, galactose, ribose, rhamnose, xylopyranose, sucrose, lactose, maltose, trehalose, cellobiose, gentiobiose, isomaltose, kojibiose, laminaribiose, mannobiose, melibiose, nigerose, rutinose, sorbital, mannitol and xylobiose. Formulations can contain, for example, about 0.001% to about 50% active osmotic modifying agent. In another related embodiment, the composition includes about 10% of osmotic modifying agent.

Chelating agents useful in tattoo removal formulations can include, without limitation, ethylene diaminetetraacetate (EDTA), desferrioxamine, clioquinol, ethylene glycol tetraacetic acid (EGTA), small hydrophobic chelators such as phenanthroline or bipyridine, hexadentate iron chelator and deferoxamine (also known as desferrioxamine, desferoxamine, DFO, DFOA or desferal). A suitable composition may contain, for example, about 0.001% to about 50% active chelating agent. In another related embodiment, the composition includes about 0.5% of chelating agent.

A formulation used to enhance tattoo removal can also include one or more of a penetration enhancer. Examples of penetration enhancers useful in formulations of the invention include vitamin E nicotinate, olive oil, propylene glycol, and polysorbate 80 (Croda Inc., Edison N.J.). Epsom salts, i.e., magnesium sulfate, and other osmotically active agents, can also be used to enhance penetration and facilitate tattoo removal.

Penetration enhancers can be active penetration enhancers or passive penetration enhancers. When olive oil is present as a lipid component to the emulsion, the olive oil also serves as a passive penetration enhancer.

A formulation used to enhance tattoo removal can also include one or more of an emulsifier, such as, for example, cetyl alcohol or glyceryl mono stearate (GMS). Emulsions can be oil in water emulsions or water in oil emulsions. Where emulsification is achieved by the use of a single emulsification agent, the emulsifier is optimally used in a range of about 0.5% to 15%. Where multiple emulsifiers are present, the combined concentration of emulsifier can be up to about 30%. Combined use of emulsifiers can provide for stiffer or looser emulsions, as known to those skilled in the art.

Where propylene glycol is present, it can serve as both a solvent, an emulsifier, and a penetration enhancer.

A formulation used to enhance tattoo removal can further include one or more component that acts as a thickener and/or binder. Examples include, without limitation, xanthum gum and hydroxyethyl cellulose (e.g., Cellosize™ QP52000H, Dow Chemical Co, Midland Mich.). In those embodiments that include xanthum gum, the concentration of xanthum gum in a range of about 1-10%. Additional thickeners, binders, and suitable polymers are known to those of ordinary skill in the art.

In some embodiments of the invention, the method includes applying an occlusive barrier to the skin region. The occlusive barrier can enhance the osmotic modifying agent's effect by creating an osmotic pressure gradient that directs interstitial fluid from the skin toward the lymphatic system. Occlusive barriers can be formed by adding an occlusive modifying agent, i.e., a chemical component, to a formulation of the invention. By way of example, an occlusive barrier can be part of the composition that dries on the skin's surface to form a non-breathable barrier, by using a component such as silicone, titanium oxide, polyvinyl acetate or polyvinyl alcohol. In other related embodiments of the invention, the occlusive barrier comprises a physical non-breathable layer including patches and wraps.

In some embodiments of the invention, administering the cell disruptor treatment includes high-energy electromagnetic radiation in the range from about 200 nanometers to about 1300 nanometers. In a related embodiment, the electromagnetic radiation may be generated in any conventional manner capable of generating an amount of energy sufficient to disrupt skin cells including any externally applied energy, derived from at least one of thermal, sonic, ultrasound, visible light, infrared light, ultraviolet light, electric, magnetic, chemical, enzymatic, mechanical, and any other type of energy.

In an embodiment of the invention, administering the cell disruptor treatment involves using electromagnetic radiation generated by a pulsed laser including, but not limited to Q-switched ruby lasers, Q-switched alexandrite lasers, and Q-switched Nd:YAG lasers (Adrain et al., Clinics in Plastic Surgery, 27, 181 (2000)). One particular embodiment involves using a Q-switched Nd:YAG laser (532 nm) a cell disruptor. Another embodiment involves using a Q-switched Nd:YAG laser (1064 nm) as a cell disruptor. Yet another embodiment involves using a Q-switched alexandrite (755 nm) laser as a cell disruptor. Other embodiments involve using a combination of lasers.

In one embodiment, administering the composition to the skin region may occur in at least one or a combination of time periods before, after, and at the same time as treating the region with a cell disruptor. In some embodiments, administering the composition occurs at least once within about 20 minutes of a treatment with the cell disruptor, for example, at least one administration from about 20 minutes before treatment with the cell disruptor to about 20 minutes after treatment with the cell disruptor, such that the vasodilator-containing product is present during operation of the cell disruptor. In some embodiments of the invention, administering the composition occurs, for example, from a single dose to multiple doses administered multiple times per day. In another embodiment, timing of application of a tattoo removal formulation should be 10 minutes before the cell disruptor, e.g., laser, treatment and also again after the treatment, with a range of time of immediately after to 60 minutes, depending on how tender the skin is after the laser treatments.

Another desirable application schedule can be one to three times a day everyday for up to one month, to maximize the movement of particles away from the tattooed area. Then after one month another cell disruption treatment can be applied and the cycle repeated.

In one embodiment, the method of removing a tattoo from a region of skin includes administering the treatment to a human. In alternative embodiments, the method of removing a tattoo from a region of skin further includes administering the treatment to non-human animals, including non-human primates, rodents, dogs, cats, horses, pigs, sheep, goats, and cows.

In alternative embodiments, the tattoo may be a fresh tattoo or a mature tattoo.

Examples of formulations useful for enhancing the removal of tattoos are set forth in Tables 1-7.

TABLE 1

| Example 1, formulation with a vasodilator | |
| --- | --- |
| Ingredient | % By wt. |
| Cetyl Alcohol | 3.00 |
| Glyceryl Mono Stearate | 3.00 |

TABLE 1-continued

| Example 1, formulation with a vasodilator | |
| --- | --- |
| Ingredient | % By wt. |
| Olive oil | 5.00 |
| Propylene Glycol | 4.00 |
| Methyl Nicotinate | 0.20 |
| Xanthan Gum | 1.00 |
| Vitamin E Nicotinate | 0.01 |
| Deionized Water | 83.79 |
| Total | 100.00% |

The formulation of Example 1 is prepared as follows. In Tank 1, weigh in the cetyl alcohol, glyceryl monostearate, olive oil, and vitamin E nicotinate and heat to 70° C. and mix until clear. Into the main tank, weigh in methyl nicotinate, and add deionized water. Mix at high speed. Disperse the xanthan gum in the propylene glycol, and add slowly into the main tank while mixing at high speed. Heat to 70° C., transfer contents in tank 1 into the main tank at 70° C. Mix for 10 minutes and then cool to room temperature.

TABLE 2

| Examples 2 and 3, formulations with vasodilator and osmotic agent | | |
| --- | --- | --- |
| Ingredients | Example 2 % By wt. | Example 3 % by wt. |
| Cetyl Alcohol | 5.00 | 5.00 |
| Glyceryl Mono Stearate | 8.00 | 8.00 |
| Olive oil | 10.00 | 10.00 |
| Methyl Nicotinate | 0.10 | 0.10 |
| Vitamin E Nicotinate | 0.01 | 0.01 |
| Cellosize ™ QP-52000H | 0.50 | 1.0 |
| Propylene Glycol | 5.00 | 5.00 |
| Polysorbate 80 | 4.00 | 4.00 |
| Epsom Salt | 15.00 | 15.00 |
| Water | 52.39 | 51.89 |
| Total | 100.00% | 100.00% |

The formulations of Examples 2 and 3 are prepared as follows. In Tank 1, weigh in cetyl alcohol, glyceryl monostearate, olive oil, and vitamin E nicotinate, and heat to 70° C. and mix until clear. In the main tank, weigh in the methyl nicotinate, polysorbate 80, Epsom salt, and water. Mix at high speed. Disperse Cellosize™ QP-52000H in propylene glycol, and add slowly into the main tank while mixing at high speed. Heat to 70° C., transfer contents in tank 1 into main tank at 70° C. Mix for 10 minutes, and then cool to room temperature.

TABLE 3

| Examples 4 and 5, use of vasodilator and occlusive barrier | | |
| --- | --- | --- |
| Ingredient | Example 4 % By wt. | Example 5 % By wt. |
| Cetyl Alcohol | 3.00 | 3.00 |
| Glyceryl Mono Stearate | 3.00 | 3.00 |
| Olive oil | 5.00 | 5.00 |
| Propylene Glycol | 4.00 | 4.00 |
| Methyl Nicotinate | 0.20 | 0.20 |
| Xanthan Gum | 1.00 | 0.5 |
| Vitamin E Nicotinate | 0.01 | 0.01 |
| Deionized Water | 60.79 | 61.29 |
| Stearoxytrimethylsilane and Stearyl alcohol | 10.00 | 10.00 |
| AluminiumAluminum Choride | 13.00 | 13.00 |
| TOTAL | 100.00% | 100.00% |

The formulations of Examples 4 and 5 are prepared as follows. In Tank 1, weigh in cetyl alcohol, glyceryl monostearate, vitamin E nicotinate, olive oil and the stearoxytrimethylsilane and stearyl alcohol, heat to 70° C., and mix until clear. In the main tank, weigh in methyl nicotinate, aluminum chloride and water. Mix at high speed. Disperse xanthan gum in propylene glycol, and add slowly into the main tank while mixing at high speed. Heat to 70° C., and transfer contents of tank 1 into the main tank at 70° C. Mix for 10 minutes, and then cool to room temperature.

TABLE 4

Examples 6 and 7, use of vasodilator, osmotic agent and occlusive barrier.

| Ingredients | Example 6 % By wt. | Example 7 % By wt. |
|---|---|---|
| Cetyl Alcohol | 5.00 | 5.00 |
| Glyceryl Mono Stearate | 8.00 | 5.00 |
| Olive oil | 10.00 | 5.00 |
| Methyl Nicotinate | 0.10 | 0.10 |
| Vitamin E Nicotinate | 0.01 | 0.01 |
| Cellosize ™ QP-52000H | 0.50 | 0.50 |
| Propylene Glycol | 5.00 | 5.00 |
| Polysorbate 80 | 4.00 | 4.00 |
| Epsom Salt | 15.00 | 10.00 |
| Stearoxytrimethylsilane and Stearyl alcohol | 10.00 | 10.00 |
| Aluminum Chloride | 13.00 | 10.00 |
| Water | 29.39 | 45.39 |
| TOTAL | 100.00% | 100.00% |

The formulations of Examples 6 and 7 are prepared as follows. In Tank 1, weigh in cetyl alcohol, glyceryl monostearate, vitamin e nicotinate, olive oil and stearoxytrimethylsilane and stearyl alcohol. Heat to 70° C. and mix until clear. In the main tank, weigh in the methyl nicotinate, polysorbate 80, aluminum chloride, epsom salt, and water. Mix at high speed. Disperse Cellosize™ QP-52000H in the propylene glycol, and add slowly into the main tank while mixing at high speed. Heat to 70° C., and transfer contents of Tank 1 into the main tank at 70° C. Mix for 10 minutes, and then cool to room temperature.

TABLE 5

Example 8, use of vasodilator and chelating agent

| Ingredient | % By wt. |
|---|---|
| Cetyl Alcohol | 3.00 |
| Glyceryl Mono Stearate | 3.00 |
| Olive oil | 5.00 |
| Propylene Glycol | 4.00 |
| Methyl Nicotinate | 0.20 |
| Xanthan Gum | 1.00 |
| Vitamin E Nicotinate | 0.01 |
| Tetra sodium EDTA | 0.50 |
| Deionized Water | 83.29 |
| TOTAL | 100.00% |

The formulation of Example 8 is prepared as follows. In Tank 1, weigh in cetyl alcohol, glyceryl monostearate, vitamin e nicotinate, and olive oil. Heat to 70° C. and mix until clear. In the main tank, weigh in methyl nicotinate, Tetra Sodium EDTA and water. Mix at high speed. Disperse the xanthan gum in the propylene glycol, and add slowly into the main tank while mixing at high speed. Heat to 70° C., transfer contents of Tank 1 into the main tank at 70° C. Mix for 10 minutes, and then cool to room temperature.

TABLE 6

Example 9, use of vasodilator, osmotic agent and chelating agent:

| Ingredients | % By wt. |
|---|---|
| Cetyl Alcohol | 5.00 |
| Glyceryl Mono Stearate | 8.00 |
| Olive oil | 10.00 |
| Methyl Nicotinate | 0.1 |
| Vitamin E Nicotinate | 0.01 |
| Cellosize ™ QP-52000H | 0.5 |
| Propylene Glycol | 5.00 |
| Polysorbate 80 | 4.0 |
| Epsom Salt | 15.00 |
| Tetra sodium EDTA | 0.50 |
| Water | 51.89 |
| TOTAL | 100.00% |

The formulation of Example 9 is prepared as follows. In Tank 1, weigh in cetyl alcohol, glyceryl monostearate, vitamin E nicotinate, olive oil, heat to 70° C., and mix until clear. In the main tank, weigh in methyl nicotinate, polysorbate 80, tetra sodium EDTA, epsom salt and water. Mix at high speed. Disperse Cellosize™ QP-52000H in propylene glycol, and add slowly into the main tank while mixing at high speed. Heat to 70° C., and transfer contents of Tank 1 into main tank at 70° C. Mix for 10 minutes, and then cool to room temperature.

TABLE 7

Examples 10 and 11, use of vasodilator, osmotic agent, occlusive barrier, and chelating agent

| Ingredients | Example 10 % By wt. | Example 11 % By wt. |
|---|---|---|
| Cetyl Alcohol | 5.00 | 5.00 |
| Glyceryl Mono Stearate | 8.00 | 3.00 |
| Olive oil | 10.00 | 5.00 |
| Methyl Nicotinate | 0.10 | 0.10 |
| Vitamin E Nicotinate | 0.01 | 0.01 |
| Cellosize ™ QP-52000H | 0.50 | 0.50 |
| Propylene Glycol | 5.00 | 5.00 |
| Polysorbate 80 | 4.00 | 4.00 |
| Epsom Salt | 15.00 | 10.00 |
| Stearoxytrimethylsilane and Stearyl alcohol | 10.00 | 10.00 |
| Aluminum Chloride | 13.00 | 10.00 |
| Tetra sodium EDTA | 0.50 | 0.50 |
| Water | 28.89 | 46.89 |
| TOTAL | 100.0% | 100.0% |

The formulations of Examples 10 and 11 are prepared as follows. In Tank 1, weigh in cetyl alcohol, glyceryl monostearate, vitamin e nicotinate, olive oil and stearoxytrimethylsilane and stearyl alcohol. Heat to 70° C. and mix until clear. In the main tank, weigh in methyl nicotinate, polysorbate 80, aluminum chloride, tetra sodium EDTA, epsom salt and water. Mix at high speed. Disperse Cellosize™ QP-52000H in propylene glycol, and add slowly into the main tank while mixing at high speed. Heat to 70° C., transfer contents in tank 1 into main tank at 70° C. Mix for 10 minutes, and then cool to room temperature.

Methods of evaluating the efficacy of the invention composition in combination with standard methods of cell disruption, such as laser treatments, to remove the tattoo.

The animal experiments used to assess the efficacy of the invention composition requires the tattooing of a single, linear 4 cm line of blue-black tattoo ink on the skin of a shaved guinea pig. One month after the tattooing of the guinea pigs, different groups of animals are subjected to different procedures to remove the visual evidence of the tattoo. All groups will receive laser treatments, one group will not be treated with any topical cream. Group two will receive a placebo lotion, such as a retail skin moisturizing lotion and the other groups will receive one or other of the invention compositions. Those groups of guinea pigs receiving the topical creams will be treated one day prior to the laser treatment with 1 gram of cream to the skin, rubbing it into the skin until it is absorbed. On day 2, all of the animals are subjected to a Q-Switched Ruby, Q-Switched Alexandrite or Q-Switched ND-YAG laser, which are standard lasers in the tattoo removal field. The choice of the laser is dictated by the effectiveness in removing different colors of tattoo inks. In the cream treatment groups, the creams will be applied by rubbing approximately 1 gram of the tattoo removal formulation into the skin until absorbed immediately after the laser treatment, and then successive applications of the tattoo removal cream are administered in a similar manner to the pre-treatment two times each day for thirty days. On day 30, a second laser treatment is given to both the untreated and the cream-treated groups, the tattoo is photographed and evaluated for the ability of the cream to enhance the removal of the tattoo image. This cycle is repeated until the tattoo is no longer visible. The time to image removal or reduction in intensity is the key measure of the success of the cream treatments as well as the reduction in the number of laser treatments required to reach this endpoint. The assessment of the efficacy of the invention cream(s) on the different colors of tattoo ink is correlated with the different laser types to serve as a general guideline for the optimized combination to remove the tattoo.

Human tattoos will be evaluated with the similar series and combinations of conditions described above, with the exception that the evaluation of tattoo removal will be done with people with existing tattoos. The level of variability of one person to the next and the complexity and color schemes used in the tattoo will require the study candidates to be categorized by the level of complexity and size of the tattoo as well as the color(s) in an effort to standardize the starting point of the image. The initial round of testing of the invention composition cream will be performed with the laser in conjunction with the invention composition cream or a placebo cream with people presenting with only blue-black tattoos. The invention composition will be applied to the laser treated area of skin within about 30 to 60 minutes following the laser treatment. Two grams of cream will be applied to the skin and rubbed until absorbed. This procedure is repeated three times each day for the course of a month, until the next laser treatment, after which the cycle can be repeated. Assessment of the efficacy of the creams and the laser treatment combinations is recorded photographically at each monthly interval. After this portion of the study is complete, further testing can be conducted on those individuals with multi-color tattoos and more complex designs using multiple types of lasers identified as suitable for those types of tattoos and also in combination with either the invention composition cream or a placebo cream to determine the advantage the use that the invention cream has over either a placebo cream or no cream at all.

The invention composition cream can be evaluated for its ability to enhance the utility of the laser to remove the image as measured by a reduced number of laser shots and time required to reduce and remove the image.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of removing a tattoo from a region of skin, the method comprising
    treating the region with a cell disruptor so as to cause cells of the skin to rupture; and
    administering to the same region a tattoo removal composition comprising
        a vasodilator,
        at least one osmotic modifying agent in an amount sufficient to draw water from cells and vasculature of the skin,
        and at least one chelating agent,
        so as to cause enlargement of blood vessels in the region, so that the action of the composition and the cell disruptor causes removal of the tattoo.

2. The method of claim 1, wherein administering the composition includes applying the composition topically to the region.

3. The method of claim 1, wherein administering the composition includes applying the composition via a transdermal patch.

4. The method of claim 1, wherein administering the composition includes injecting the composition into the region of skin with a suitable medical device.

5. The method of claim 4, wherein injecting the composition includes using any one of a hypodermic needle, a syringe, and a needleless injection device.

6. The method of claim 1, wherein administering the composition includes delivering the composition by one or more of a topical formulation, a patch-like device, an iontophoresis device, a sonophoresis device, and an injection.

7. The method of claim 1, wherein administering the composition includes covering the region with a non-breathable occlusive barrier that dries on the skin.

8. The method of claim 1, wherein administering the composition includes covering the region with a physical non-breathable occlusive barrier.

9. The method of claim 1, wherein treating the region with the cell disruptor includes using externally applied energy.

10. The method of claim 9, wherein treating the region with the cell disruptor includes using a laser.

11. The method of claim 9, wherein treating the region with the cell disruptor includes using externally applied energy derived from at least one of thermal, sonic, ultrasound, visible light, infrared light, ultraviolet light, electric, magnetic, chemical, enzymatic, mechanical, and any other type of energy.

12. The method of claim 1, wherein treating the region with the cell disruptor takes place after administering the composition.

13. The method of claim 1, wherein treating the region with the cell disruptor takes place before administering the composition.

14. The method of claim 1, wherein treating the region with the cell disruptor takes place coincident with administering the composition.

15. The method of claim 1, wherein administering the composition occurs in a single dose.

16. The method of claim 1, wherein administering the composition occurs in one of multiple doses and multiple times per day.

17. The method of claim 1, wherein administering the composition includes administering it to one of a human and a non-human animal.

\* \* \* \* \*